United States Patent [19]
Prou

[11] Patent Number: 5,089,012
[45] Date of Patent: Feb. 18, 1992

[54] SURGICAL SUTURE, IN PARTICULAR FOR STERNOTOMY CLOSURE

[75] Inventor: Philippe Prou, Roinville Sous Auneau, France

[73] Assignee: Ethicon, Inc., Somerville, N.J.

[21] Appl. No.: 578,171

[22] Filed: Sep. 6, 1990

[51] Int. Cl.$^5$ .............................................. A61B 17/00
[52] U.S. Cl. ..................................... 606/224; 606/225
[58] Field of Search ................................. 606/224–227

[56] References Cited

U.S. PATENT DOCUMENTS

| | | | |
|---|---|---|---|
| 1,613,206 | 1/1927 | Souttar | 606/226 |
| 2,591,063 | 4/1952 | Goldberg | 606/226 |
| 3,311,110 | 3/1967 | Singerman et al. | 606/226 |
| 3,762,418 | 10/1973 | Wasson | 606/226 |
| 3,835,912 | 9/1974 | Kristensen et al. | 606/226 |
| 4,372,293 | 2/1983 | Vijil-Rosales | 606/225 |

FOREIGN PATENT DOCUMENTS

| | | | |
|---|---|---|---|
| 1088711 | 4/1984 | U.S.S.R. | 606/225 |
| 2188237 | 9/1987 | United Kingdom | 606/216 |

Primary Examiner—Stephen C. Pellegrino
Assistant Examiner—Gary Jackson

[57] ABSTRACT

A suture includes an essentially rigid needle connected to a monofilament which is essentially plastically deformable in flexion, wherein the needle (1) and the monofilament (2) are joined by means of a filiform intermediate element (3) which is essentially elastically deformable in flexion. The intermediate element is very advantageously a twisted multi-strand cord and is preferably attached to the needle and/or the monofilament by autogenous welding.

11 Claims, 1 Drawing Sheet

U.S. Patent  Feb. 18, 1992  5,089,012
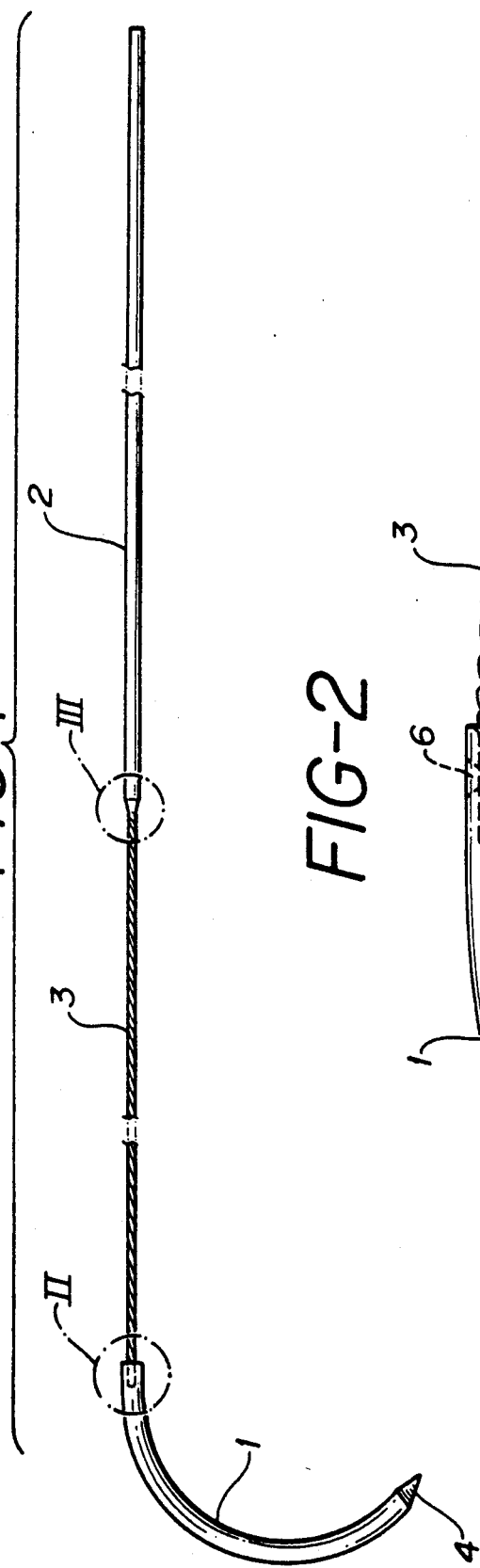
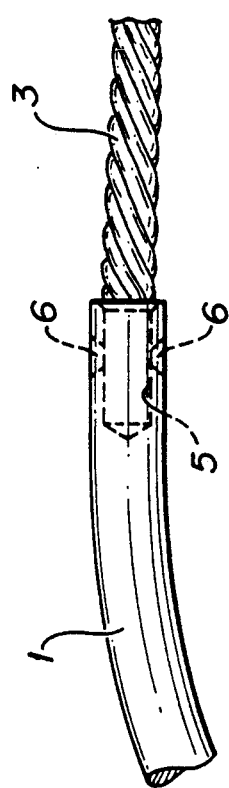
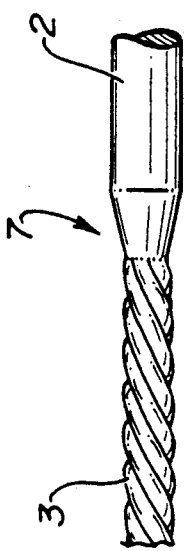

SURGICAL SUTURE, IN PARTICULAR FOR STERNOTOMY CLOSURE

The present invention relates to the surgical sutures used in the case of surgery necessitating a prior sternotomy, such as open-heart surgery (sternotomy closure).

The sutures used for surgery of this type must in the first place be designed to permit an easy penetration of the dense tissues despite their great resistance to penetration. Moreover, they must be able to provide a very great mechanical resistance given the considerable stresses to which they will be subjected during a long period following surgery; such is typically the case with the sternum which has been ligatured in order to permit the reconstitution of the osseous tissue between the two halves separated during the sternotomy.

The surgical sutures used hitherto for this purpose comprise a curved needle which is very rigid and very sharp at one of its ends and is prolonged at its other end by way of a monofilament strand of stainless steel providing great mechanical resistance to traction. However, this monofilament is very plastically deformable in flexion so that the tissues can be sutured correctly from the surgical point of view. An example of a known surgical suture of this type comprising a needle fixed on a stainless steel monofilament is described and illustrated in the document GB-A-2,188,237.

Sutures of this type generally exhibit a mechanical weakness at the point where the monofilament strand is fixed to the needle (generally by crimping of punching): indeed, given the essentially rigid nature of the needle and the essentially deformable nature of the monofilament, after several manipulations of the needle a rupture of the monofilament is sometimes observed at the point where it is crimped on the needle, or in the vicinity of this point. This rupture is occasioned by the concentration of the stresses at the junction point between the needle and the monofilament during the manipulations.

In order to prevent this occurrence, when manipulating the needle in order to carry out the suture, the surgeon must take care not to stress the monofilament excessively in its part adjacent to the needle, which can sometimes be difficult given the anatomical disposition of the members to be sutured and the restrictions on space in the operating field.

The present invention proposes a novel suture making it possible to overcome this disadvantage.

Indeed, as will be seen, the suture according to the invention is protected from any risk of rupture during manipulation by virtue of its structure, while at the same time being particularly easy for the surgeon to use; thus, the surgeon can perform his work quickly and without risk.

To this end, the suture according to the invention, which comprises an essentially rigid needle connected to a monofilament which is essentially plastically deformable in flexion, wherein the needle and the monofilament are joined by means of a filiform intermediate element which is essentially elastically deformable in flexion and consist of a twisted multi-strand cord.

The intermediate element is preferably attached to the needle and/or the monofilament by autogenous welding.

The document U.S. Pat. No. 4,372,293 describes a system for plastic surgery comprising a needle fixed to the first end of a strip whose second end is itself fixed to a stainless steel filament. This document is not in any way concerned with the surgical sutures for sternotomy closure and, thus, the very particular and specific problems posed by these sutures given the very great mechanical resistance required for the elements composing them. Furthermore the system proposed in the document U.S. Pat. No. 4,372,293 constitutes an implant for plastic surgery rather than a surgical suture.

The document U.S. Pat. No. 2,591,063 describes a surgical suture for ophthalmic surgery.

An example of embodiment of the invention will now be given.

FIG. 1 is a view of the suture according to the invention, showing the various elements constituting this suture.

FIG. 2 is a detailed view (indicated by II in FIG. 1) of the junction between the needle and the multi-strand cord.

FIG. 3 is a detailed view (indicated by III in FIG. 1) of the junction between the multi-strand cord and the monofilament.

The suture according to the invention (FIG. 1), comprises a needle 1 and a monofilament 2 which are elements known per se.

The needle 1 is a needle having a circular curvature, formed from a round body presenting a triangular end 4 which is very sharp and of cross-section smaller than the body of the needle, in order to reduce tissue traumatism.

This needle is made of a material which is rigid (in order to prevent it from deforming) and resistant (in order to prevent the point from becoming blunt) for example a stainless steel having undergone suitable heat treatment and careful polishing.

The monofilament 2 is made of a material which provides for great mechanical resistance to traction (low ductility), which nevertheless permits a ready plastic deformation so as to be easily curved in order to carry out the suture, and which is neutral from the point of view of any tissue reactions.

It may be formed, for example, from a filament of perfectly calibrated diameter, of stainless steel with a smooth, perfectly polished and brilliant appearance.

A characteristic feature of the invention is that, instead of the monofilament and the needle being fixed directly to one another (by crimping or punching) as was the case in the prior art, these two elements are joined by way of a filiform intermediate element 3 by means of which it is possible to ensure the transition, from the point of view of mechanical properties, between the needle 1 and the monofilament 2.

This intermediate element 3 is a filament made from a material which is essentially elastically deformable, this ensuring the transition between the needle 1, which is essentially rigid, and the monofilament 2, which is essentially plastically deformable.

This intermediate element 3 very advantageously consists of a twisted multi-strand cord, which presents several advantages:
- on account of its regularity, its outer profile is as similar as possible to a monofilament;
- it has a resistance to traction comparable to that of a monofilament, but in contrast has a flexibility (possibility of elastic deformation) which permits latitude of movement to the manipulation of the needle by the surgeon;
- finally, its quality renders it neutral in use through tissues.

The material of this multi-strand cord is advantageously a stainless steel.

FIG. 2 shows the detail of the assembly between the needle 1 and the multi-strand cord 3.

In order to permit this assembly, the needle 1 is, for example, drilled at its end with a blind axial bore 5 of a diameter slightly larger than that of the multi-strand cord. The multi-strand cord is then introduced inside the bore 5, and this assembly is then positioned on an autogenous welding station, for example by YAG laser welding, which produces two diametrically opposed welding points 6 in the assembly zone.

FIG. 3 shows the detail of the assembly between the multi-strand cord 3 and the monofilament 2.

In order to assemble these two elements, they can be presented, for example, end to end, the end of the monofilament being brought into contact with the multi-strand cord before being immobilized. The two elements are then joined by autogenous welding (here again, preferably by laser welding) in such a way as to flow the weld reinforcement of the monofilament over the multi-strand cord, this operation being carried out on the whole periphery of the cord and monofilament.

As can be seen at 7 in FIG. 3, this assembly procedure does not cause any increased thickness or rough edges and makes it possible to achieve a profile presenting a perfectly regular and continuous transition between the cylindrical profile of the multi-strand cable and that of the monofilament.

In practice, this suture has proven particularly effective, in particular as regards:

its resistance to traction, which is notably greater than that of a traditional suture with assembly by crimping or punching;

the decreased risks of rupture between the needle and the filament, this permitting an omnidirectional traction of the needle on the filament, with complete safety.

The diameters and lengths of the various elements can be extremely variable as a function of the applications envisaged. For a needle 48 mm in length and 1.4 mm in diameter, there may be provided, for example, a multi-strand cord 150 mm in length and 0.74 mm in diameter, for a monofilament 450 mm in length and 0.78 or 0.88 mm in diameter.

Of course, these dimensions are given only by way of example, the only important point being that the diameter of the multi-strand cord should be slightly smaller, (preferably by at least 0.04 mm) than that of the monofilament 2 in order to permit a suitable welding without increased thickness.

I claim:

1. A surgical suture for sternotomy closure, comprising an essentially rigid needle connected to a monofilament which is essentially plastically deformable in flexion, wherein the needle (1) and the monofilament (2) are joined by means of a filiform intermediate element (3) which is essentially elastically deformable in flexion and consists of a twisted multi-strand cord, the diameter of the twisted multi-strand cord being smaller than that of the monofilament.

2. The suture as claimed in claim 1, in which the intermediate element is attached to the needle by autogenous welding.

3. The suture as claimed in claim 1, in which the intermediate element is attached to the monofilament by autogenous welding.

4. The suture as claimed in claim 1, wherein the twisted multi-strand cord is made of steel.

5. The suture as claimed in claim 1, wherein the monofilament (2) is made of steel.

6. The suture as claimed in claim 1, wherein the diameter of the multi-strand (3) is smaller than that of the monofilament (2), by at least 0.04 mm.

7. The suture as claimed in claim 1, wherein the assembly of the twisted multi-strand cord (3) on the monofilament (2) is effected by placing these two elements end to end, until they come into contact, and by carrying out laser welding on the whole periphery of the cord (3) and the monofilament (2), in such a way as to flow the weld reinforcement of the monofilament (2) over the multi-strand cord.

8. The suture as claimed in claim 1, wherein the multi-strand cord (3) has a length of the order of 150 mm, while the monofilament (2) has a length of the order of 450 mm.

9. The suture as claimed in claim 1, wherein the diameter of the multi-strand cord is of the order of 0.74 mm, while the diameter of the monofilament (2) is of the order of 0.78 to 0.88 mm.

10. The suture as claimed in claim 1, wherein the multi-strand cord (3) is fixed on the needle (1) by laser welding.

11. The suture as claimed in claim 1, wherein the needle (1) is provided with a blind axial bore (5) in which the end of the multi-strand cord (3) is engaged, and wherein the latter is fixed on the needle by laser welding, preferably in the form of two diametrically opposed welding points (6).

* * * * *